(12) United States Patent
Gebing (10) Patent No.: US 7,618,809 B2
(45) Date of Patent: Nov. 17, 2009

(54) MICROARRAYER WITH COAXIAL MULTIPLE PUNCHES

(76) Inventor: Ronald A. Gebing, 817 Fridinger Mill Rd., Westminster, MD (US) 21157

( * ) Notice: Subject to any disclaimer, the term of this patent is extended or adjusted under 35 U.S.C. 154(b) by 782 days.

(21) Appl. No.: 11/384,872

(22) Filed: Mar. 20, 2006

(65) Prior Publication Data

US 2006/0216781 A1 Sep. 28, 2006

Related U.S. Application Data

(60) Provisional application No. 60/664,539, filed on Mar. 23, 2005.

(51) Int. Cl.
*C12M 1/36* (2006.01)
*C12M 1/38* (2006.01)
*C12M 3/00* (2006.01)

(52) U.S. Cl. ............... 435/286.2; 435/40.52; 435/309.1

(58) Field of Classification Search .............. 435/286.2, 435/40.52, 309.1
See application file for complete search history.

(56) References Cited

U.S. PATENT DOCUMENTS

| | | | |
|---|---|---|---|
| 4,654,989 A | 4/1987 | Fleming | 40/427 |
| 4,684,613 A | 8/1987 | Barrere et al. | 435/301 |
| 4,820,504 A | 4/1989 | Battifora | 424/3 |
| 4,914,022 A | 4/1990 | Furmanski et al. | 435/7 |
| 4,979,093 A | 12/1990 | Laine et al. | 364/167.01 |
| 5,002,377 A | 3/1991 | Battifora et al. | 350/535 |
| 5,355,304 A | 10/1994 | DeMoranville et al. | 364/413.02 |
| 5,355,439 A | 10/1994 | Bernstein et al. | 395/82 |
| 5,614,415 A | 3/1997 | Markin | 436/48 |
| 5,675,715 A | 10/1997 | Bernstein et al. | 395/82 |
| 5,700,637 A | 12/1997 | Southern | 435/6 |
| 5,746,855 A | 5/1998 | Bolles | 156/64 |
| 5,804,384 A | 9/1998 | Müller et al. | 435/6 |
| 5,994,133 A | 11/1999 | Meijs et al. | 435/395 |
| 6,103,192 A | 8/2000 | Stapleton et al. | 422/50 |
| 6,103,518 A * | 8/2000 | Leighton | 435/286.3 |
| 6,136,592 A | 10/2000 | Leighton | 435/288.7 |
| 6,165,709 A | 12/2000 | Friend et al. | 435/4 |
| 6,251,601 B1 | 6/2001 | Bao et al. | 435/6 |
| 6,258,541 B1 | 7/2001 | Chapkin et al. | 435/6 |
| 6,335,163 B1 | 1/2002 | Sharon | 435/6 |
| 6,383,801 B1 | 5/2002 | Leighton | 435/286.3 |
| 6,406,840 B1 | 6/2002 | Li et al. | 435/1.3 |
| 6,534,307 B1 | 3/2003 | Muraca | 435/286.2 |
| 6,582,967 B2 | 6/2003 | Muraca | 436/174 |
| 6,699,710 B1 * | 3/2004 | Kononen et al. | 435/283.1 |
| 2002/0106626 A1 * | 8/2002 | Muraca | 435/1.3 |
| 2002/0146813 A1 * | 10/2002 | Leighton | 435/286.3 |
| 2002/0192702 A1 | 12/2002 | Kononen et al. | 435/6 |
| 2003/0138827 A1 | 7/2003 | Kononen et al. | 435/6 |
| 2003/0186353 A1 * | 10/2003 | Erickson et al. | 435/40.52 |
| 2004/0197897 A1 | 10/2004 | Leighton | 435/286.2 |
| 2006/0121596 A1 | 6/2006 | Chaumat | 435/283.1 |

* cited by examiner

*Primary Examiner*—Jill Warden
*Assistant Examiner*—Danielle Henkel
(74) *Attorney, Agent, or Firm*—Hooker & Habib, P.C.

(57) ABSTRACT

A microarrayer apparatus for constructing arrays of biological material from donor cores obtained from at least one donor block and placing the donor cores in an embedding medium carried by at least one recipient block. The apparatus includes a donor punch, a recipient punch, and a stylus mounted for independent coaxial movement along a common punch axis. The recipient punch cooperates with the stylus when ejecting a donor core from the donor punch to minimize deformation of the donor core.

23 Claims, 10 Drawing Sheets

MICROARRAYER WITH COAXIAL MULTIPLE PUNCHES

This application claims priority to U.S. Provisional Patent Application No. 60/664,539 filed Mar. 23, 2005.

FIELD OF INVENTION

The invention relates to an apparatus for the construction of biological arrays in an embedding medium, namely, an apparatus capable of creating paraffin-embedded biological arrays as well as frozen biological arrays.

BACKGROUND OF INVENTION

Researchers at the National Human Genome Research Institute (NHGRI) at the National Institutes of Health (NIH), in collaboration with the University of Tampere in Finland and the University of Basel in Switzerland, have developed a new research tool which they call the "tissue chip." The tissue chip has enabled researchers to distinguish among subgroups of cancer patients and eventually predict which subgroups will respond to specific therapies. Such detailed new information can then be used to identify critical molecules for development of cancer therapies.

The tissue chip is a thin section of a biological microarray that permits massive parallel processing of biological samples, making it possible for researchers to simultaneously compare an array of biological samples for molecular markers, DNA, RNA, and proteins in tissues from hundreds or thousands of samples. As many as one thousand individual samples can be studied in a single biological microarray, thus making it practical to simultaneously test thousands of biological samples when researchers would traditionally analyze one sample at a time. The power of this technology is expected to reduce analysis time and reduce the costs of reagents used in the analysis thus accelerating research while reducing costs.

Early methods of generating biological microarrays generally include removing tissue slices or cores from paraffin blocks and re-embedding these. For example, Battifora, U.S. Pat. No. 4,820,504 teaches forming multiple tissue samples into rods, bundling the rods into a casing, embedding the encased rods in paraffin and sectioning them. Although the method arrays multiple tissue samples, the method requires a high degree of manual dexterity, and often makes it difficult to find and identify particular samples of interest.

Battifora, U.S. Pat. No. 5,002,377 describes cutting tissue samples into strips, positioning the strips into parallel grooves in a mold, and embedding the strips in paraffin. The strips are stacked to form an embedded block comprising of multiple tissue samples. This method has improved the ability to identify the location of samples but is still very time consuming and is performed manually.

In order to construct biological microarrays in an efficient and precise manner, several apparatus have been recently described to transfer a multitude of biological materials into an array form within an embedding medium. All of the art describes using two separately mounted punches: the donor punch for coring and transferring the donor sample and the recipient punch for preparing a receptacle to receive the donor sample. The outside diameter of the recipient punch is nearly equivalent to the inside diameter of the donor punch.

Much of the disclosed art describes apparatus to manipulate the two punches, donor and recipient, relative to each other and with respect to a donor and recipient block. The donor punch is precisely positioned over the recipient block when transferring the sample to the predetermined receptacle with minimal, if not any, repositioning.

Leighton, U.S. Pat. No. 6,103,518 describes an apparatus that positions two punches, the recipient punch and the donor punch, on a displaceable mechanism such that each punch will be precisely positioned against stops or detents. The stops or detents require initial and periodic adjustment in order to maintain the concentricity of the two punches while in their operational positions and after punch replacement.

Leighton, U.S. Pat. No. 6,383,801 describes an apparatus that drives the two separate punches separately in the Z-axis, and periodically recalibrates the punch concentricity in order to properly align to donor punch to a receptacle made previously by the recipient punch. The device requires an offset measurement sensor, and efficiency is reduced by the subsequent measurement and correction times.

Chasse et al., U.S. patent application Publication 20030017446 also describes a similar situation where a calibration process is required between the donor punch and the recipient coring device in order to properly align to donor punch to a receptacle made previously by the recipient punch. Again, an offset measurement sensor and subsequent measurement and correction times are required.

Leighton, U.S. Pat. No. 6,468,783 and Leighton, U.S. patent application Publication 20040197897 each describe an apparatus with a mechanism for automatically changing two or more punches in and out of a holder on the Z-axis. The mechanism will align the two respective punches concentrically. But the time, however small, to locate a punch, grip, and move to the desired location for operation reduces the efficiency of the device. The mechanism and the grippers required to change the punches is mechanically complex.

Kononen et al., U.S. Pat. No. 6,699,710, the entirety of which is incorporated herein by reference, describes a first embodiment apparatus for creating tissue microarrays. A donor punch is positioned relative to a donor block to core a sample from a region of interest as identified by positioning a reference slide over the donor block. The punch is lowered to cut the core and raised to removed the core of interest. The donor block is replaced with the recipient block containing an array of receptacles and the punch apparatus is repositioned to be above a predetermined receptacle. The core is deposited into the receptacle using a stylus.

Kononen et al. teaches that the recipient block consists of an array of receptacles produced in a similar manner to the coring of the donor block prior to the donor transferring process. The coring of array receptacles, however, produces poor positional results as the density of the array increases and the diameter of the core decreases. The embedding media is not perfectly solid and does not cut cleanly; a first cored and unfilled receptacle is more likely to be displaced or distorted by an adjacent receptacle coring than if the first receptacle was filled prior to the second receptacle coring.

Kononen et al. also discloses a second embodiment apparatus for creating tissue microarrays. The second apparatus is an automated device that continues the use of two separate donor and recipient punches. The punches are mounted such that they can be positioned below a single stylus during operation so that the same stylus is aligned and inserted into the punches. The mismatch in punch diameters with the same stylus distorts the donor core during deposition into the receptacle. Distortion increases as donor core size decreases with higher density tissue microarrays.

Thus there is a need for an improved microarrayer for constructing biological arrays in an embedding medium. The improved microarrayer should be less complex in construction and more efficient in operation. The improved microarrayer should enable a receptacle in a recipient block be filled prior to forming an adjacent receptacle, and deformation of the donor core should be minimized during deposition into the receptacle.

SUMMARY OF THE INVENTION

The invention is an improved microarrayer for constructing biological arrays in an embedding medium. The improved microarrayer is less complex and more efficient than known microarrayers. The improved microarrayer enables a receptacle in a recipient block be filled prior to forming an adjacent receptacle, and deformation of the donor core is minimized during deposition into the receptacle.

An apparatus in accordance with the present invention is suitable for constructing arrays of biological material from donor cores obtained from at least one donor block and placing the donor cores in an embedding medium carried by at least one recipient block. The apparatus includes a donor punch configured for coring the donor block, a recipient punch configured for coring the recipient block, and a stylus configured to remove cores from the donor and recipient punches.

A support platform supports a donor block and a recipient block, the support platform defining an X-Y plane. A punch platform extends in the Z-direction away from the support platform. The punch platform and the support platform are displaceable in the X and Y directions with respect to one another for positioning the punch platform with respect to the support platform.

Each of the donor and recipient punches and the stylus are movably mounted on the punch platform for independent movement along the Z-direction towards and away from the support platform. The recipient punch, the donor punch and the stylus are arranged on the punch platform for coaxial movement along a common Z-axis.

During operation, the relative positions of the recipient punch, the donor punch, and the stylus in the X-Y directions remains unchanged with respect to one another during operation of the apparatus. This reduces the complexity of the apparatus as compared to conventional microarrayers that physically move the donor and recipient punches to and away from a common punch axis, and increases efficiency by eliminating the transit time required to move the punches to and from the punch axis.

Furthermore, the coaxial punches do not require operational adjustments due to manufacturing tolerances and the need for an offset measurement sensor. Subsequent measurement and correction times are eliminated.

In a preferred embodiment of the present invention the recipient punch and the stylus cooperate to remove a donor core from the donor punch. This effectively eliminates the mismatch between the outer diameter of the stylus and the inner diameter of the donor punch, and substantially eliminates or minimizes possible distortion of the donor core during ejection from the donor punch.

Another embodiment of the present invention has the support platform including a donor block platform vertically spaced away from a recipient block platform. This enables the donor block and recipient block to be both placed on the punch axis during operation of the machine without the punch platform moving vertically between operations on the donor block and the recipient block.

Microarrayers in accordance with the present invention can be designed to be manually operated, semi-manually operated, or be under fully-automatic operation. The control system can automatically place the punch axis over the donor block or recipient block for coring and transfer operations.

Other objects and features of the invention will become apparent as the description proceeds, especially when taken in conjunction with the accompanying ten drawing sheets illustrating two embodiments of the invention.

DETAILED DESCRIPTION OF THE PREFERRED EMBODIMENTS

Figure 1:
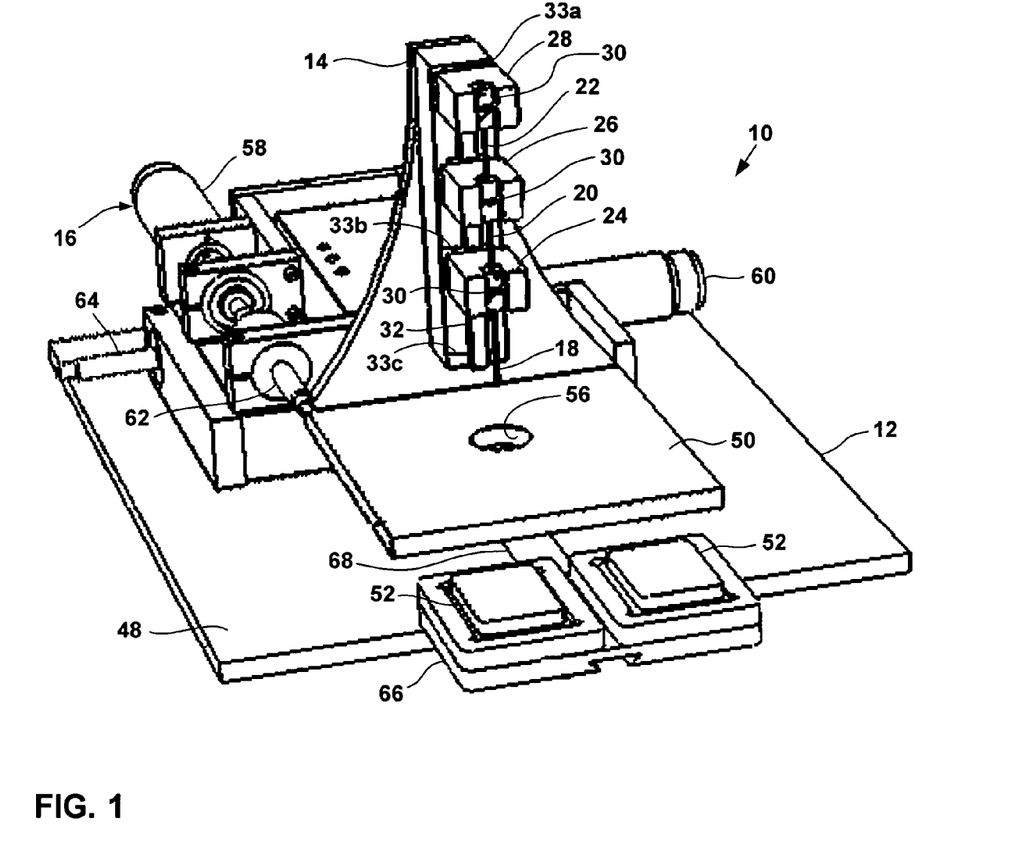
FIG. 1 illustrates a first embodiment microarrayer in accordance with the present invention prior to punching a receptacle in a recipient block, the punches and stylus of the microarrayer in their ready positions and a recipient block holder in its access position.

FIG. 1 illustrates a first embodiment microarrayer 10 in accordance with the present invention. Microarrayer 10 constructs arrays of biological material from donor cores obtained from at least one donor block, placing the donor cores in an embedding medium carried by at least one recipient block. The recipient and donor blocks are supported on a fixed support platform 12 that defines an X-Y plane. Extending away from the support platform 12 in the Z-direction is a punch platform 14. Punch platform 14 is stationary with respect to support platform 12 in the Z-direction, but is movable relative to the support platform in the X and Y directions by a platform drive assembly 16. Drive 16 displaces the punch platform 14 in the X and Y directions to selectively position the platforms 12, 14 with respect to one another.

Mounted on the punch platform 14 is a donor punch 18, a recipient punch 20, and a stylus 22. Each of the punches 18, 20 and stylus 22 are movably mounted on the punch platform by a respective donor punch slide 24, recipient punch slide 26, and stylus slide 28 for movement towards and away from the support platform 12. Donor punch slide 24 is adjacent the support platform 12, recipient punch slide 26 is adjacent donor punch slide 24, and stylus slide 28 is adjacent recipient punch slide 26 farthest from the support table 12. Radially-enlarged hubs 30 surround the upper end of each punch 18, 20 and stylus 22. Each hub 30 mounts a punch or stylus to its respective slide while permitting rotation of the punch or stylus about its longitudinal axis.

The slides 24-28 are independently movable and guided for vertical movement in the Z-direction by a guide rail 32 extending vertically along the punch platform 14. Travel of stylus slide 28 along rail 32 is limited by upper and lower stylus stops 33a and 33b (shown only in FIG. 1) that define the ends of upward and downward movement of the stylus slide. Downward movement of donor punch slide 24 is limited by a punch stop 33c (shown only in FIG. 1), while upward movement of donor punch slide 24 is limited by contact with recipient punch slide 26. Travel of recipient punch slide 26 is limited by contact with either donor punch slide 24 or stylus slide 28.

Springs 35a, 35b, and 35c maintain slides 24-28 in a ready position or neutral position shown in FIG. 1 when not in use. See FIG. 10. Spring 35a extends between punch platform 14 and donor punch slide 24. Spring 35b extends between punch slides 24, 26. Spring 36b extends between recipient punch slide 26 and stylus slide 28. Springs 35 urge the slides to return to the ready position after a displacement from the ready position.

Figure 7A:
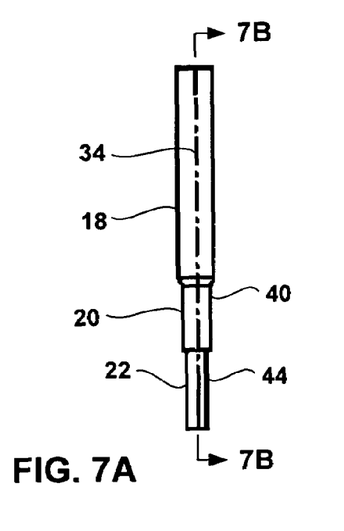
FIG. 7A is a front view of the coaxial punches and stylus used in the microarrayer shown in FIG. 1.
Figure 7B:
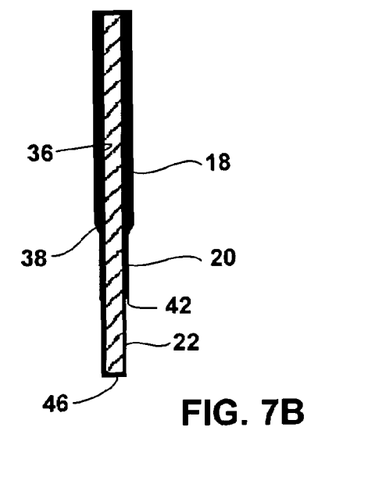
FIG. 7B is a sectional view taken along line 7B-7B of FIG. 7A.

Punches 18, 20 and stylus 22 are elongate members arranged on the punch platform 14 with member axes arranged for coaxial movement along a common Z-axis or vertical punch axis 34 towards and away support platform 12. See FIGS. 7A and 7B, which illustrate the relationship between the donor punch 18, recipient punch 20, and stylus 22 (note that FIGS. 7A and 7B do not illustrate the components in a normal operating position).

During operation of microarrayer 10, stylus 22 is received within recipient punch 20, and recipient punch 20 is received within donor punch 18 as will be described in greater detail below. The longitudinal axes or centerlines of punches 18, 20 and stylus 22 remain coaxial with each other along the common punch axis 34 during all operations of microarrayer 10.

Donor punch 18 is a tubular member having an inner diameter 36 that establishes the diameter of the donor core cut from the donor block. The lower end of the punch 18 is sharpened with a bevel 38 on its outer diameter to provide a cleanly-cut donor core. Recipient punch 20 is a tubular member having an outer diameter 40 that establishes the diameter of the receptacle cut from the recipient block. The lower end of the punch 20 is sharpened with a bevel 42 on its inner diameter to provide a cleanly-cut receptacle. The outer diameter 40 of recipient punch 20 is less than the inner diameter 36 of donor punch 18 to permit recipient punch 20 to slide or move inside donor punch 18. Stylus 22 is a solid cylindrical member having an outer diameter 44 sized to closely fit within the inner diameter of the recipient punch 20 and has a flat lower surface 46.

Referring back to FIG. 1, support platform 12 includes a recipient block platform 48 and a vertically spaced-apart donor block platform 50. The upper surface of recipient block platform 48 defines a first X-Y plane for supporting at least one recipient block 52. The upper surface of donor block platform 50 defines a second X-Y plane for supporting at least one donor block 54 (see FIG. 4). Donor block platform 50 is spaced away from the recipient block platform 48 towards the punches 18, 20 with sufficient clearance to enable a recipient block to fit beneath the donor block platform 50. A through-hole 56 in the donor block platform 50 enables access to a recipient block beneath the donor block platform 50 by the punches 18, 20 when coring a recipient block or placing a donor core in a recipient block receptacle.

Platform drive assembly 16 includes a pair of motors 58, 60 that move punch platform 14 along orthogonal shafts 62, 64 attached to the support platform 12 and extending in the X and Y directions respectively. Other platform drives are known and can be readily adapted for use in the present invention.

FIGS. 1-3 and FIGS. 8A-8D illustrate operation of the microarrayer 10 to punch a receptacle in a recipient block. As shown in FIG. 1, punches 18, 20 and stylus 22 are positioned in their ready positions prior to beginning the operation. A recipient block 52 is placed in a recipient block holder 66 (in the illustrated embodiment holder 66 can hold two recipient blocks). Holder 66 holds and positions the recipient blocks on recipient platform recipient block platform 48. Holder 66 slides along a rail 68 between an access position shown in FIG. 1 and an operational position in which the recipient blocks are under the donor block platform 50. Detents (not shown) hold holder 66 in each of the two positions. When holder 66 is in the access position, its location out from under the donor block platform 50 allows for compete inspection or removal and installation of the recipient blocks.

A recipient block 52 is mounted in holder 66 and holder 66 is placed in its operational position to position recipient block 52 under the donor block platform 50. Recipient block 52 is of conventional construction and carries an embedding media, such as OCT, paraffin, or other material suitable for embedding biological materials. Block 52 can an initially be an un-cored block.

Drive assembly 16 moves the punch platform 14 as necessary to center the punch axis 34 directly over the intended receptacle site on the recipient block 52. Donor punch slide 24 is lowered against punch stop 33c to locate the lower end of the donor punch 18 just at the surface of the recipient block. See FIG. 8A, which illustrates the donor punch 18 just at the surface of recipient block 52. Because there is great variability in the height of actual recipient blocks, the location of punch stop 33c is adjustable to compensate for such differences in height.

Figure 2:
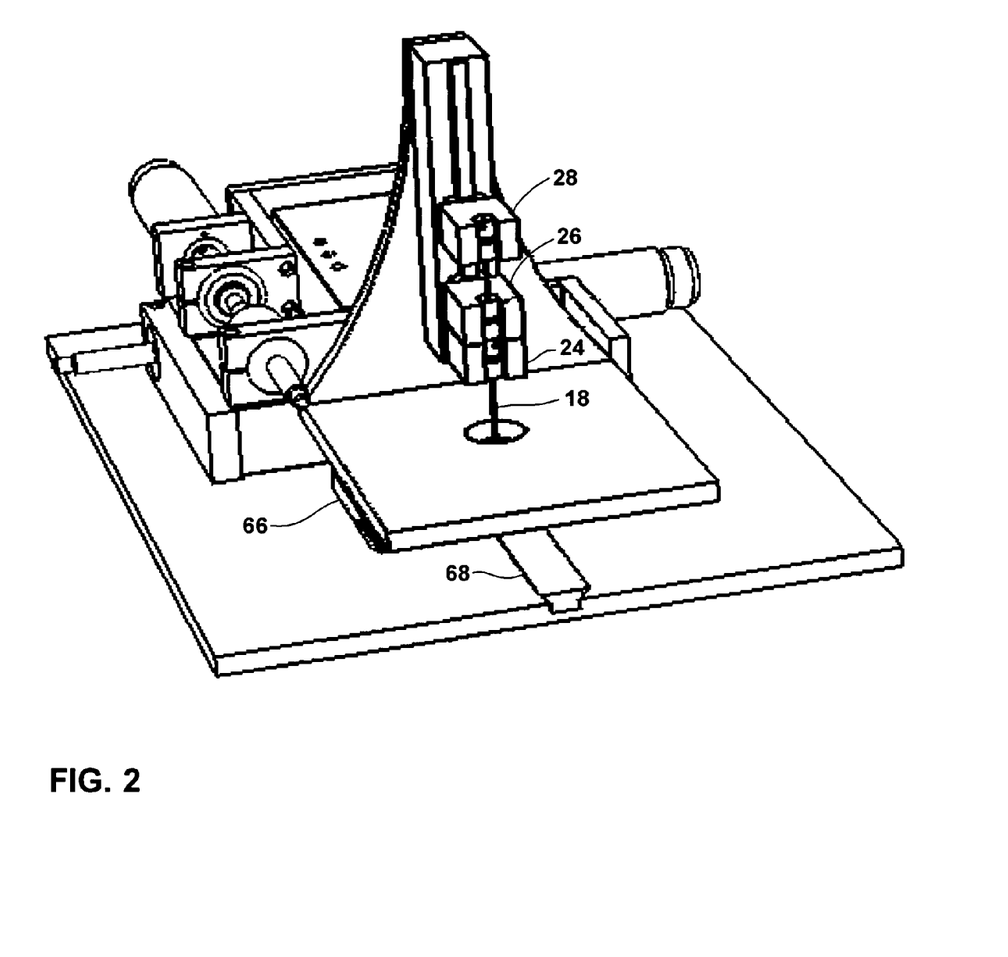
FIG. 2 illustrates the recipient block holder in an operational position and the recipient punch slide lowered to core the receptacle of the recipient block.
Figure 8A:
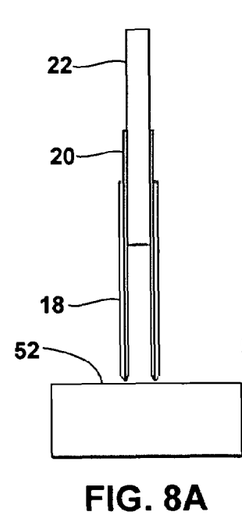
FIGS. 8A-8D illustrate the punches and stylus forming a receptacle in the recipient block and expelling the receptacle core.
Figure 8B:
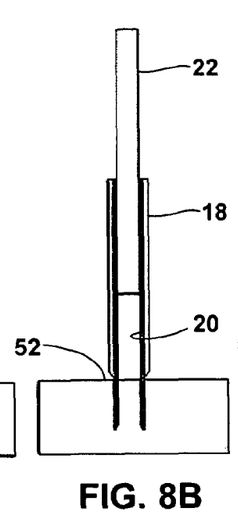
Figure 8C:
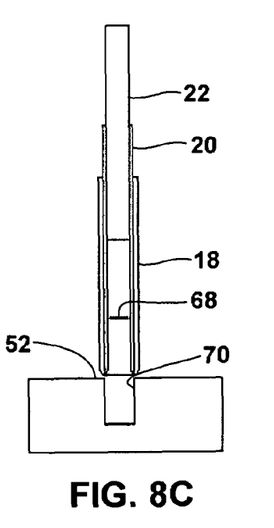

Recipient punch slide 26 is then lowered against donor punch slide 24. Recipient punch 20 moves within donor punch 18. When punch slide 26 abuts donor punch slide 24 as shown in FIG. 2 and comes to a hard stop, recipient punch 20 is in a predetermined axial relationship with donor punch 18 as shown in FIG. 8B. The lower end of recipient punch 20 has entered the recipient block 52 to core the receptacle block to a predetermined depth. Recipient punch slide 26 is raised and a receptacle core 68 is held within recipient punch 20 and removed from the receptacle block 52 to form a receptacle 70. See FIG. 8C. Recipient punch 20 withdraws back into donor punch 18 as they begin to both move up and away from the recipient block 52.

Figure 3:
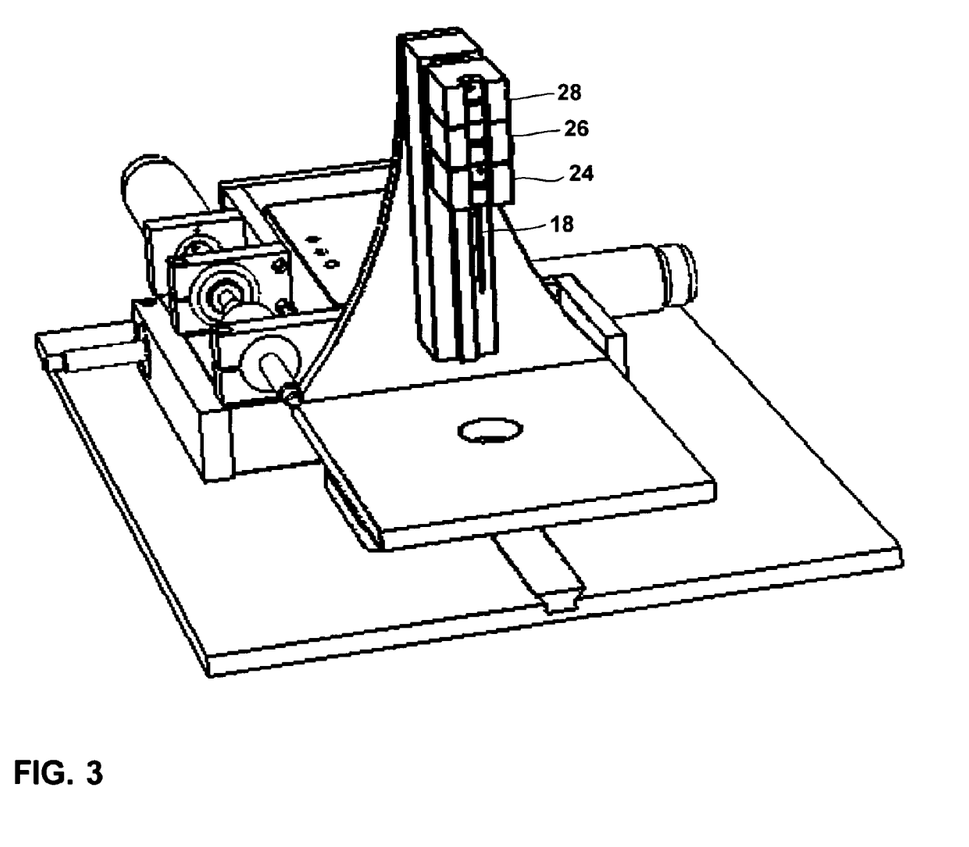
FIG. 3 illustrates raising the donor punch slide, the recipient punch slide, and the stylus slide to expel a recipient core from the recipient punch.
Figure 8D:
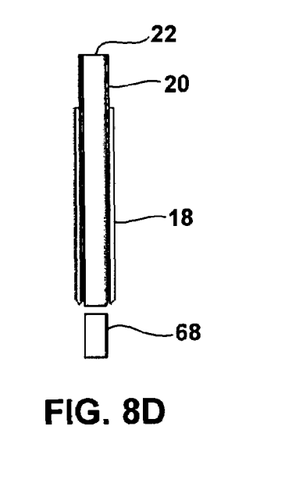

Donor punch slide 24 is then raised to raise the recipient punch slide 26 and force the stylus slide 28 against the upper stylus stop 33a as shown in FIG. 3. In this position stylus 22 extends into the recipient punch 20 and slightly protrudes from the lower end of the recipient punch to fully expel receptacle core 68 from recipient punch 20 as shown in FIG. 8D. Core 68 can be discarded, and slides 24, 26, and 28 are returned to their ready positions.

Figure 4:
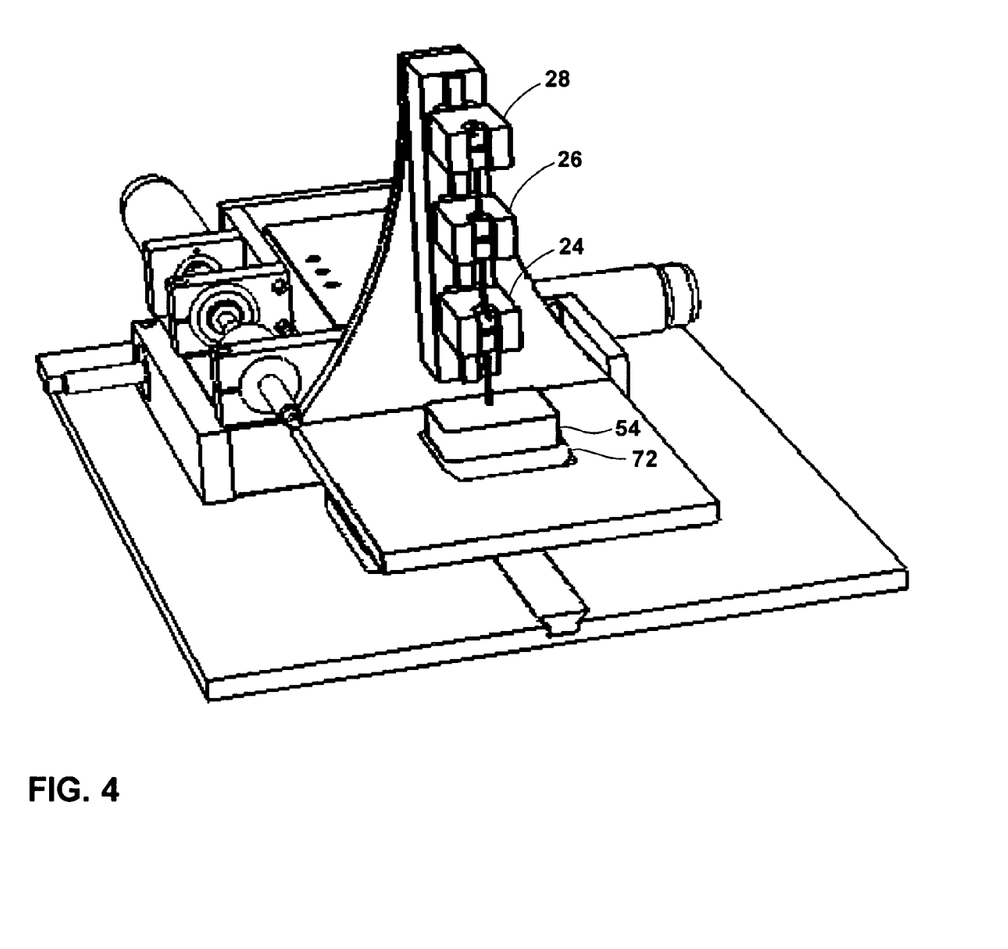
FIG. 4 illustrates the microarrayer with the donor block in place, the donor punch slide lowered to core the donor block for sample transfer.

FIGS. 4-6 and FIGS. 9A-9E illustrate operation of the microarrayer 10 to core a donor block 54 and place the donor core into recipient block receptacle 70. As shown in FIG. 4, donor block 54 is placed in a donor block holder 72 (in the illustrated embodiment holder 72 holds one recipient block). Illustrated holder 72 fits into hole 56 to hold and position the donor block on donor block platform 50. Drive assembly 16 moves the punch platform 14 as necessary to center the punch axis 34 directly over the intended donor site on donor block 54.

Figure 9A:
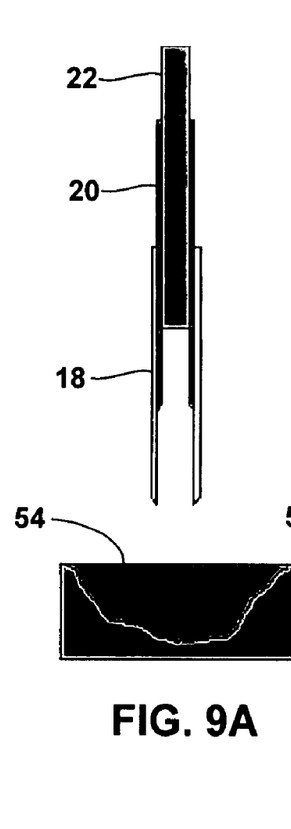
FIGS. 9A-9E illustrate cutting a donor core and transferring the donor core into the recipient block receptacle shown in FIG. 8C.
Figure 9B:
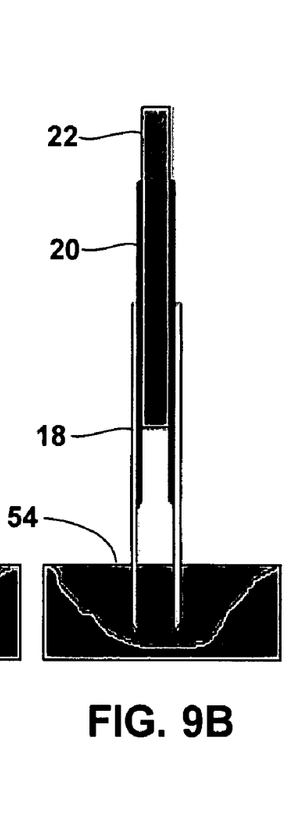
Figure 9C:
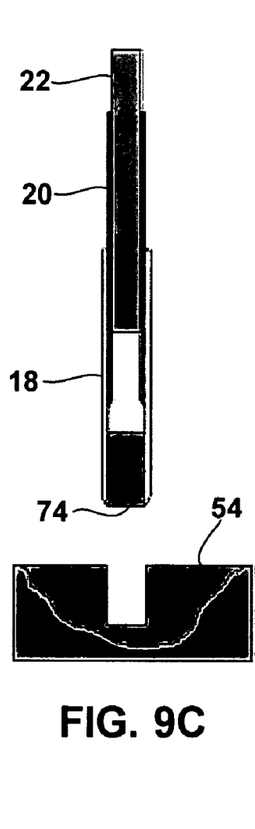
Figure 9D:
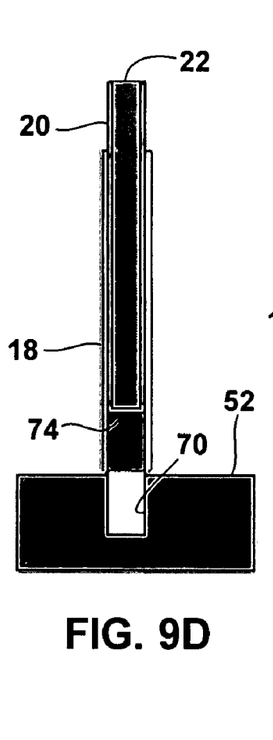

FIG. 9A illustrates the relative positions of the donor punch 18, recipient punch 20, and stylus 22 in their ready positions over donor block 54 on donor block platform 50. Donor punch slide 24 is lowered from its ready position against the lower punch stop to insert donor punch 18 into donor block 54 as shown in FIG. 3 and FIG. 9B. The springs 35 keep the recipient punch slide 26 spaced away from donor punch slide 24 as the donor punch slide 24 moves towards the donor block 54. Donor punch slide 24 then returns to its ready position to return donor punch 18 to the ready position as shown in FIG. 9C with a donor core 74 contained in the donor punch 18.

After removal of donor core 74 from the donor block, holder 72 with donor block 54 is removed to re-open hole 56 for access to recipient block 52. In other embodiments holder 72 can be moved laterally on donor platform 50 in a manner similar to moving holder 66. Drive assembly 16 moves the punch platform 14 again if necessary to re-center the punch axis 34 directly over receptacle 70.

With slides 24-28 in their ready position, stylus slide 28 is lowered to extrude the donor core 74 into receptacle 70. Stylus slide 28 contacts recipient punch slide 26, and both slides 26, 28 move downward together. Spring 35b between the donor punch slide 24 and recipient punch slide 26 pushes down on the donor punch slide 22 and concurrently urges the donor punch slide 22 downwards until it reaches punch stop 33c.

Figure 5:
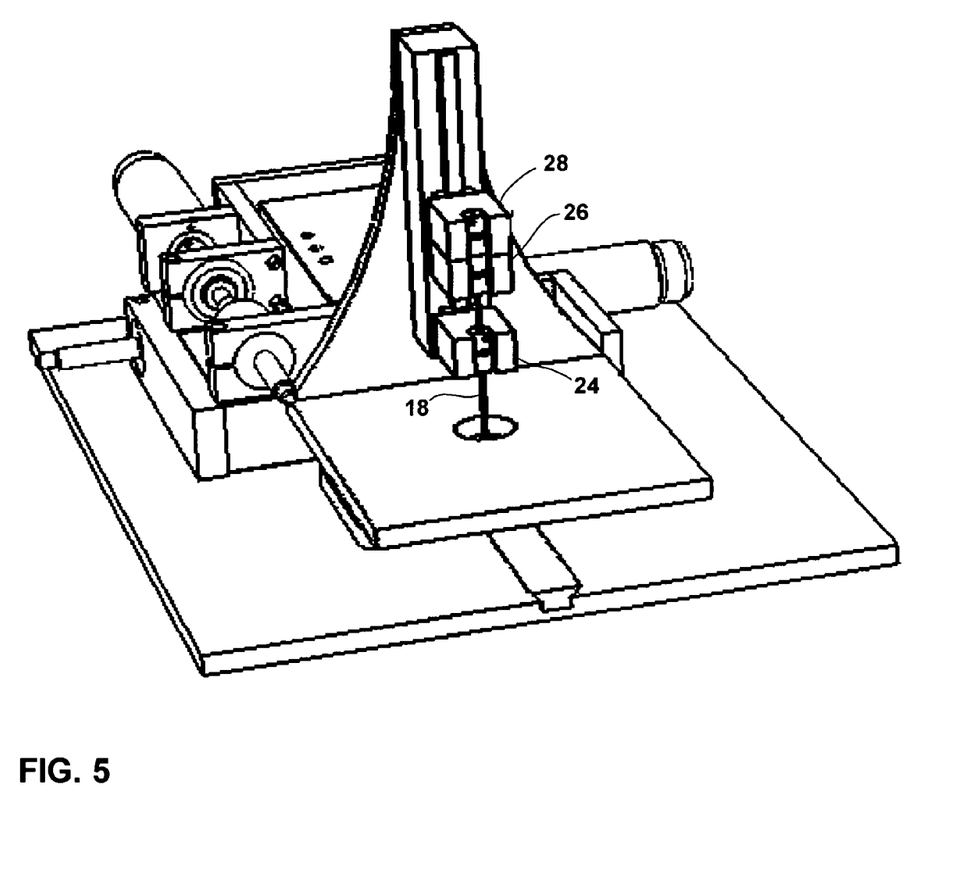
FIG. 5 illustrates lowering the stylus slide to extrude the donor core into the recipient block.

FIG. 5 illustrates the donor punch slide 24 reaching the punch stop, the lowermost limit of travel of slide 24. Recipient punch slide 26 is still spaced from donor punch slide 24. In this position, shown in FIG. 9D, the lower end of donor punch 18 stops just at the upper surface of the recipient block 52.

Further downward movement of stylus slide 28 forces further downward movement of recipient punch slide 26, and moves the stylus 22 and recipient punch 20 further into the donor punch 18. When the stylus slide 28 reaches the lower stylus stop 33b, the lower end of the stylus 22 has pushed the donor core 74 out of donor punch 18 and into receptacle 70. See FIG. 9E. Stylus slide 28 is halted by the lower stylus stop at just the right position to deposit the donor core either below the surface of the recipient block or just above. The position of the lower stylus stop 33b is adjustable by the user to "fine tune" the insertion level of donor cores into the receptacles.

Figure 9E:
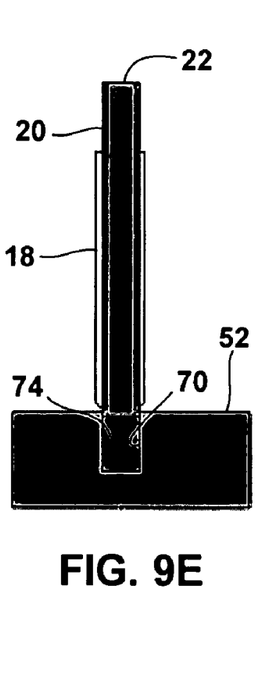

As shown in FIG. 9E, the lower end of the recipient punch 20 also cooperates with the lower end of the stylus to push or extrude donor core 74 out of donor punch 18. This effectively eliminates the mismatch between the outer diameter of stylus 22 and inner diameter 36 of donor punch 18, and substantially eliminates possible distortion of the donor core 74 during ejection of the donor core that might occur if stylus 22 were used alone (the softer the donor core, the greater the chance of such distortion).

Outer diameter 40 of recipient punch 20 is less than the inner diameter 36 of donor punch 18 to enable a sliding or running fit between the two punches 18, 20. Therefore the outer diameter of receptacle 70 is slightly smaller than the outer diameter of donor core 74, defining an interference fit between the receptacle and the donor core. Because of this interference fit, donor core 74 fits snugly in receptacle 70 with less risk of falling out of the receptacle.

Figure 6:
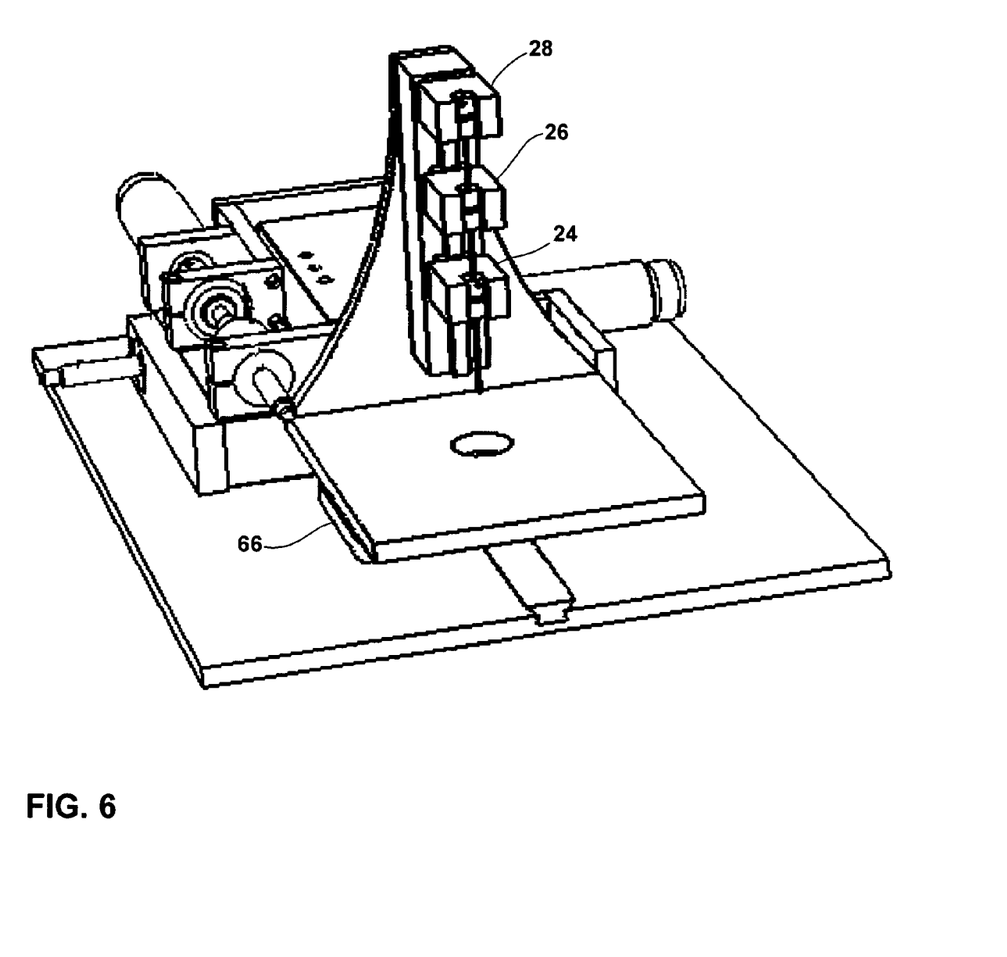
FIG. 6 is similar to FIG. 1 but illustrates the punch slides and the stylus slides in a ready position after the donor core transfer and before the punch platform is moved to center the punch axis over the next receptacle location in the recipient block.

After extrusion of the donor core, slides 24-28 return to their ready positions as shown in FIG. 6 to repeat the process of coring the recipient block, coring the donor block, and placing the donor core into a receptacle in the recipient block. When used with an initially fresh or un-cored recipient block, microarrayer 10 can cut all the receptacles in the receptacle block before cutting donor cores from donor blocks, or can be used to sequentially cut and fill each receptacle.

In a second embodiment, drive assembly 16 can be under automatic control to automatically move and position the punch platform 14 to form the array of receptacles in a recipient block or to move between a donor block coring position to the next recipient block coring position.

Figure 10:
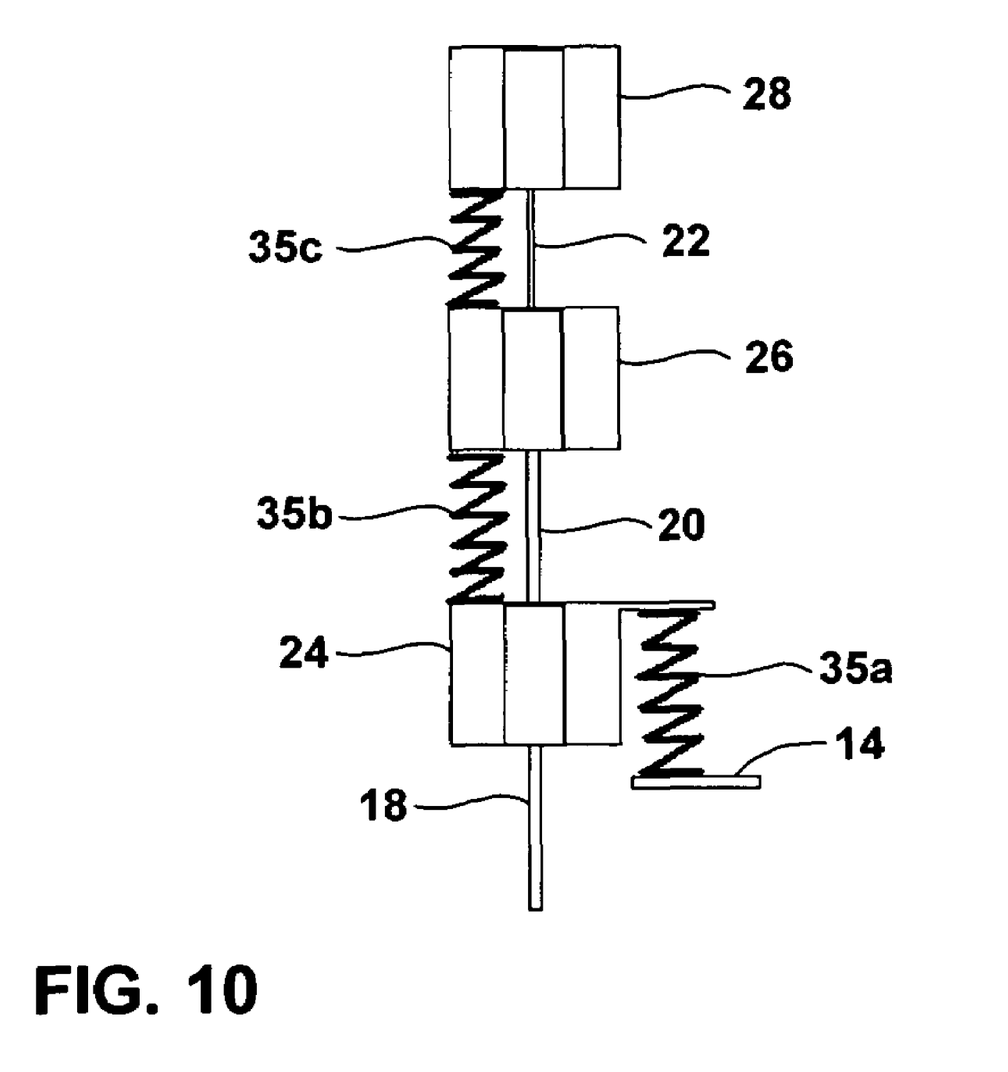
FIG. 10 illustrates the arrangement of punch and stylus slides and springs of the microarrayer shown in FIG. 1 with the slides in their ready position.
Figure 11:
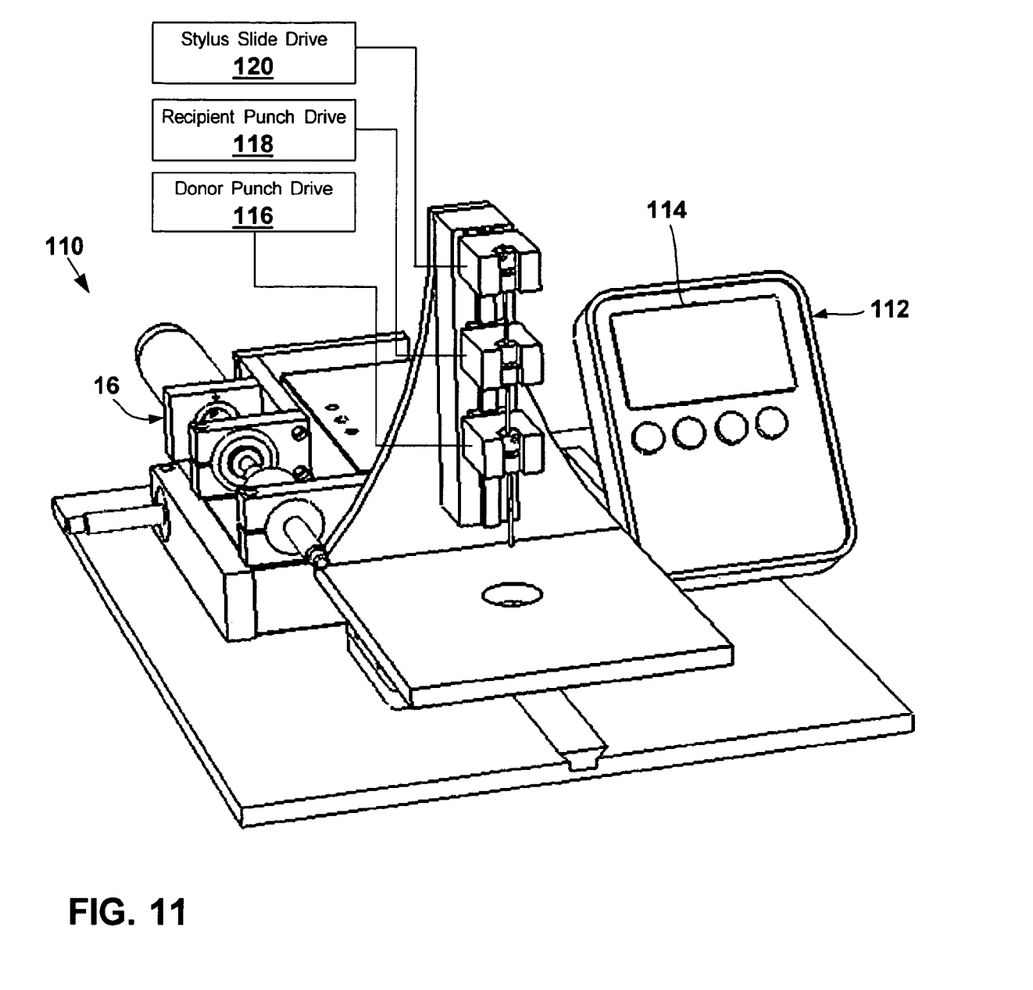
FIG. 11 is a view similar to FIG. 1 of a second embodiment microarrayer in accordance with the present invention that includes an automated control system that controls movement of the punch platform, punch slides, and stylus slide.

FIG. 10 illustrates a second microarrayer 110 in accordance with the present invention. Microarrayer 110 is otherwise identical to microarrayer 10 but includes a computerized control system 112 having a user interface represented by a display screen 114 and operatively coupled to drive assembly 16 and drives 116, 118, and 120 that drive the donor punch slide, recipient punch slide, and the stylus slide respectively. Pneumatic, hydraulic, and electric slide drives are known and can be readily adapted for use in the present invention.

Control system 112 automatically controls the drives and motors and responds to user feedback received from a keypad, mouse, stylus, touch screen, or the like, and automatically controls the relative X-Y position of the support platform 12 and punch platform 14 to sequentially align the punch axis with the different receptacle locations on a recipient block.

Control system 112 also controls motion of the punches and stylus along the punch axis, and can set the upper and lower travel limits of the slides in lieu of or in addition to mechanical stops. Compensation for variations in donor or recipient block thicknesses can also be made. The use of springs can be eliminated if all slide movement will be generated by slide drives controlled by the control system.

The illustrated microarrayers 10, 110 have vertically spaced-apart recipient block and donor block platforms 48, 50 that permit the recipient block and punch platform to remain stationary and maintain Z-axis alignment while a donor core is being obtained. In other embodiments the recipient block and donor block can be supported on a single, flat support surface, and the punch platform moved in the X-Y direction to move between the recipient block and the donor block. In such embodiments the punch platform 14 can be vertically movable with respect to the support surface to change vertical spacing between the punches and the recipient block and donor block as needed. In yet other of such embodiments the punch platform 14 can be stationary in the Z-direction but the travel lengths of the slides can change during coring and extruding operations. Changes in stroke length or the ready positions of the slides are preferably accomplished by using slide drives under the control of a control system rather than adjusting the position of mechanical stops or limits.

While I have illustrated and described preferred embodiments of my invention, it is understood that this is capable of modification, and I therefore do not wish to be limited to the precise details set forth, but desire to avail myself of such changes and alterations as fall within the purview of the following claims.

What I claim as my invention is:

1. An apparatus for constructing arrays of biological material from donor cores obtained from at least one donor block and placing the donor cores in an embedding medium carried by at least one recipient block, the apparatus comprising:

a support platform for supporting a donor block and a recipient block, the support platform defining an X-Y plane;

a punch platform extending in the Z-direction away from the support platform, the punch platform and the support platform displaceable in the X and Y directions with respect to one another for positioning the punch platform with respect to the support platform;

a donor punch configured for coring the donor block, a recipient punch configured for coring the recipient block, and a stylus configured to remove cores from said donor and recipient punches;

wherein the outer diameter of the recipient punch is less than the inner diameter of the donor punch to permit the recipient punch to slide or move inside the donor punch, and the stylus having an outer diameter sized to closely fit within the inner diameter of the recipient punch each of said donor punch, recipient punch, and stylus movably mounted on the punch platform for independent movement along the Z-direction towards and away from the support platform; and the recipient punch, the donor punch and the stylus arranged on the punch platform for coaxial movement along a common Z-axis, whereby the relative positions of the recipient punch, the donor punch, and the stylus in the X-Y directions remains effectively unchanged with respect to one another during operation of the apparatus.

2. The apparatus of claim 1 comprising a first slide, a second slide, and a third slide, each slide movably mounted to the punch platform for movement along the Z-axis;

the donor punch attached to the first slide, the recipient punch attached to the second slide, and the stylus attached to the third slide, the first slide adjacent the support platform, the second slide between the first slide and the third slide.

3. The apparatus of claim 2 wherein each of said donor punch, recipient punch, and stylus are rotatably attached to the punch platform to permit rotation of the punches and stylus about the Z-axis.

4. The apparatus of claim 1 wherein the punch platform and the support platform are fixed in the Z-direction with respect to each other.

5. The apparatus of claim 1 wherein the punch platform comprises a donor block platform and a recipient block platform, the recipient block platform and the donor block platform spaced apart from each other in the Z-direction.

6. The apparatus of claim 5 wherein the donor block platform is between the recipient block platform and the donor punch.

7. The apparatus of claim 1 wherein the recipient punch and the stylus are arranged to both engage a donor core held in the donor punch to cooperatively eject the donor core from the donor punch.

8. The apparatus of claim 1 wherein the donor punch is a tubular member, the recipient punch is a tubular member, and the stylus is configured to simultaneously be at least partially in both the recipient punch and the donor punch when ejecting a core from at least one of the recipient punch and the donor punch.

9. The apparatus of claim 1 wherein the donor punch is movable towards the support platform to a first position corresponding to a surface of a recipient core to be cored by the recipient punch;

the recipient punch is movable towards the support platform to a second position when the donor core is in the first position; and the recipient punch is configured to extend through the donor punch and into the recipient block to core the recipient block when the recipient punch is in the second position.

10. The apparatus of claim 9 wherein the recipient punch is movable away from the recipient block from the second position to a third position to withdraw a recipient core from the recipient block;

the stylus is movable along the punch axis to a fourth position when the recipient block is in the third position; and the stylus extends into the recipient punch to engage and eject the recipient core when the recipient punch and stylus are in their respective third and fourth positions.

11. The apparatus of claim 10 wherein the donor punch is movable away from the recipient core to a fifth position wherein the stylus also extends into the donor punch and ejects the recipient core from the donor punch when ejecting the recipient core from the recipient punch.

12. The apparatus of claim 1 wherein the donor punch is movable to a first position along the Z-axis with respect to the support platform to extend into the donor block to core the donor block, and the recipient punch is movable to a second position along the Z-axis with respect to the support platform spaced away from the first position to extend into the recipient block to core the recipient block.

13. The apparatus of claim 1 comprising a plurality of drives and a control system for said drives wherein each of said donor punch, recipient punch, and stylus are driven by a respective drive under control of the control system for movement along the Z-axis.

14. The apparatus of claim 1 comprising adjustable stops that adjustably limit travel of the donor punch towards the support platform, and adjustably limit travel of the stylus towards and away from the support platform.

15. The apparatus of claim 1 comprising at least one spring operatively connecting the donor punch, the recipient punch, and the stylus to urge each of said punches and stylus to a respective neutral position along the Z-axis when displaced from said neutral position.

16. A method of constructing an array of biological material from donor cores obtained from at least one donor block and placing the donor cores in an embedding medium carried by a recipient block, the method comprising the steps of:

(a) providing a recipient block on a support platform defining an X-Y plane, and a recipient punch, the recipient punch configured for coring a receptacle in the recipient block, the recipient punch defining a punch axis extending in the Z-direction that is stationary with respect to the recipient punch;

(b) moving the recipient punch along the punch axis into the recipient block for coring the recipient block;

(c) moving the recipient punch along the punch axis and out of the recipient block, the recipient punch retaining the recipient core to define a receptacle in the recipient block;

(d) expelling the recipient core from the recipient punch;

(e) providing a donor block on the support platform and a donor punch, the donor punch configured for coring a donor core from the donor block;

(f) moving the donor punch along the punch axis and into the donor block for coring the donor block;

(g) moving the donor punch along the punch axis and out of the donor block, the donor block retaining the donor core;

(h) moving the donor punch along the punch axis to the receptacle formed in the recipient block; and (i) ejecting the donor core from the donor punch and into the receptacle to place the donor core in the recipient block.

17. The method of claim 16 wherein step (b) comprises the steps of:

(j) moving the donor punch to a predetermined position along the punch axis with respect to the recipient block to define a limit of travel of the recipient punch towards the recipient block; and (k) moving the recipient punch towards the recipient block to its limit of travel, the recipient punch thereby extending into the recipient block to core the recipient block.

18. The method of claim 16 wherein step (i) comprises the step of:

(j) moving the recipient punch towards the donor core in the donor punch to engage the donor core and urge the donor core out of the donor punch.

19. The method of claim 18 wherein step (i) further comprises the steps of:

(k) providing a stylus;

(l) moving the stylus along the punch axis towards the donor core in the donor punch to engage the donor core and cooperate with the recipient punch in urging the donor core out of the donor punch.

20. The method of claim 19 wherein step (d) comprises the step of:

(j) moving the stylus along the punch axis towards the recipient core to engage the recipient core and urge the recipient core out of the recipient punch.

21. The method of claim 16 wherein the recipient punch and the donor punch are cooperatively sized to define an interference fit between the receptacle and the donor core when the donor core is in the receptacle.

22. The method of claim 16 wherein step (b) comprises the step of moving the recipient punch to a first position along the punch axis to core the recipient punch, and step (f) comprises the step of moving the donor punch to a second position along the punch axis to core the donor block, the second position relatively spaced away from first position.

23. The method of claim 16 wherein each receptacle is filled with a donor core before another receptacle is formed in the recipient block.

\* \* \* \* \*